United States Patent [19]
Shieh

[11] Patent Number: 5,391,274
[45] Date of Patent: Feb. 21, 1995

[54] METHODS FOR CONTROLLING ELECTROOSMOTIC FLOW IN COATED CAPILLARY ELECTROPHORESIS COLUMNS

[75] Inventor: Chia-Hui Shieh, Irvine, Calif.
[73] Assignee: Beckman Instruments, Inc., Fullerton, Calif.
[21] Appl. No.: 138,324
[22] Filed: Oct. 18, 1993
[51] Int. Cl.⁶ .................... B01D 57/02; B01D 61/42
[52] U.S. Cl. ................................................ 204/180.1
[58] Field of Search ........................... 204/180.1, 182.8

Primary Examiner—John Niebling
Assistant Examiner—Edna Wing
Attorney, Agent, or Firm—William H. May; P. R. Harder; Janis C. Henry

[57] ABSTRACT

Methods for controlling and varying electroosmotic flow in coated capillary electrophoresis columns under electrophoretic conditions are disclosed. The methods described herein involve varying the concentration of a multi-valent buffer compound in electrophoresis buffer compositions in order to control the electroosmotic flow in capillary columns having interior surfaces coated with charged organic coatings. Increasing the concentration of a multi-valent buffer compound which has a charge opposite the charge of the organic coating, in the electrophoresis buffer results in a decrease in electroosmotic flow. Decreasing the concentration of a multi-valent buffer compound results in an increase in electroosmotic flow. The ability to control electroosmotic flow provides enhanced resolution and optimizes separations of electrophoresis sample components.

18 Claims, 5 Drawing Sheets

METHODS FOR CONTROLLING ELECTROOSMOTIC FLOW IN COATED CAPILLARY ELECTROPHORESIS COLUMNS

BACKGROUND OF THE INVENTION

1. Field of the Invention

The present invention relates generally to capillary columns having charged interior surface coatings and electrophoretic separation methods for their use. More particularly, the present invention involves methods for controlling electroosmotic flow in capillary electrophoresis columns having charged interior surface coatings by varying the concentration of buffer compounds which interact with the charged coatings.

2. Description of Relevant Art

Electrophoretic separation techniques have been utilized for years to separate molecules according to differences in the effective charge of the molecules, and/or according to differences in the molecular size of the molecules. Up until recently electrophoretic separations were conducted in gel slabs or open gel beds which were typically fabricated of polyacrylamide gel material. More recently capillary electrophoresis techniques combined with photometric detection methods have allowed the automation and rapid quantitative analysis of molecules. High revelation separations of molecules having different effective charges have been achieved by applying electrophoretic principles to buffer filled or gel filled narrow capillary tubes.

Typically, capillary columns used in capillary electrophoresis are fabricated of lengths of silica tubing having diameters on the order of 25 $\mu$m to 200 $\mu$m and lengths from about 10 to 200 cm. The buffer and gel separation mediums are pumped directly into the column interiors and electrophoretic techniques are used to separate numerous types of molecules including peptides, proteins, and oligonucleotides, nucleic acids and other charged molecular species. Moreover, the field is continually expanding with respect to the types and sizes of molecules which can be separated and detected using capillary electrophoresis procedures.

The advantages associated with capillary electrophoresis are numerous. Quantitative information can be achieved with very small sample sizes, and the amount of gel or buffer consumed is minuscule. Furthermore, the time required for the separations is sharply reduced, and the technique lends itself to automation and electronic data storage and data manipulation. Significantly, capillary electrophoresis is associated with certain phenomenon which are not present in tradition slab gel electrophoresis. One of these is the now familiar electroosmotic flow phenomenon characterized by bulk flow of buffer solutions toward one of the electrodes.

Electroosmotic flow is generated by the ionization of silanol functionalities on the surface of silica capillary tubing. The ionization results in a layer of protons in the electrophoretic buffer solution at the surface of the silica tubing. In the presence of an electric field the layer of protons resembles a positively charged column of fluid which migrates toward the cathode, causing a general bulk movement of the buffer medium. Advantageously, electroosmotic flow can be utilized in many applications to improve electrophoretic separations. For example, when the electrophoretic migration of the molecules being separated is in the opposite direction to that of electroosmotic flow, the net effect is an increase in effective column length.

Whether or not electroosmotic flow is advantageous for any particular separation, it is desirous to be able to control the flow. One method to minimize or to control electroosmotic flow, is to provide silica capillary tubing coated on the inside with a polymeric material in order to control the degree to which ionization of the surface silanol groups occurs. In general these coatings have served their intended purpose. However, there is an ongoing need for improved coatings and methods for using electroosmotic flow control to aid in electrophoretic separations.

Coated capillary columns are utilized typically to eliminate or substantially reduce electroosmotic flow during electrophoretic separation. However, interior surface capillary coatings can be designed so that separations using these coated capillaries actually have a characteristically higher electroosmotic flow compared with other coated or noncoated capillaries. In particular, for many applications, it would be desirous to utilize capillary electrophoresis columns having a particular coating and be able to increase or decrease the electroosmotic flow which is characteristic to that particular coated column.

The ability to vary electroosmotic flow in coated capillary column is especially advantageous when sample components are difficult to resolve and decreasing or increasing electrophoretic flow provides improved resolution. In cases where the sample components differ significantly in net charge, then increasing the electroosmotic flow can shorten the analysis time. If the sample components have similar net charge, then the ability to decrease the electroosmotic flow in order to enhance the small differences in the electrophoretic mobility is particularly advantageous.

Another problem associated with the capillary electrophoresis is the tendency for sample components to adhere to the wall of the capillary tubing, and in particular silica tubing. This is especially true in the case of small charged molecules which are easily attracted to reactive silica functionalities. When small peptides and amines are present in electrophoretic separation mediums, they interact. both electrostatically and hydrophobically with the capillary wall. The result is a decrease in separation efficiency and undesirable band broadening which gives erroneous separation data.

Coated capillary columns help minimize or eliminate undesirable capillary wall and sample interactions. For separating peptides and proteins, it has been suggested that charged polymeric coatings be applied. However, the ability to vary the electroosmotic flow using these coated capillary columns is minimal.

Accordingly, it is an objective of the present invention to provide methods for controlling electroosmotic flow in coated capillary columns.

It is additionally an objective of the present invention to provide methods for controlling electroosmotic flow in coated capillary electrophoresis columns and simultaneously reduce or eliminate interactions between sample components and the interior capillary wall.

It is additionally an objective of the present invention to provide capillary electrophoretic separation methods for the separation and resolution of a variety of charged molecules.

SUMMARY OF THE INVENTION

The present invention satisfies the above-identified objectives by providing methods for varying electroosmotic flow in capillary columns having charged interior surface coatings by varying the concentration of the electrophoretic buffer. Advantageously, the present invention provides for the use of coated capillary columns which contribute to the reduction in the amount of interaction between sample constituents and the interior surface of the capillary column while simultaneously providing methods for varying the electroosmotic flow in the coated column. Moreover, the present invention contributes to enhancing user control over the degree of the separation resolution of sample components and the length of time required for effective electrophoretic separations and analysis. Practicing the methods of the present invention results in improved analytical separations for a number of compounds including amines, peptides, and proteins.

Accordingly, the methods of the present invention involve controlling electroosmotic flow in a capillary electrophoresis column in order to enhance the electrophoretic resolution of components in a sample during electrophoresis. An exemplary method includes first providing a capillary column fabricated of a length of tubing having an interior surface coated with an organic multi-valent ionic compound. The coated column has a characteristic electroosmotic flow during electrophoretic separation conditions using a multi-valent electrophoretic buffer composition having a separation first buffer concentration. The next step involves introducing a buffer composition which includes a multi-valent compound into the coated capillary column. The buffer composition has a second multi-valent buffer compound concentration such that to increase the characteristic electroosmotic flow the second multi-valent buffer compound concentration is smaller than the first buffer concentration, and to decrease the characteristic electroosmotic flow the second multi-valent buffer compound concentration is greater than the first buffer concentration. Then introducing the sample composition into an end of the length of tubing and applying an electric field across a cathode reservoir positioned at one end of the tubing and an anode reservoir positioned at the other end of the tubing causes the electroosmotic flow to vary from the electroosmotic flow characteristic of the coated column.

Exemplary coated capillary columns useful in the practice of the present invention include silica capillary columns having a coating of a multi-valent positively charged compound such as a multi-functional amine compound in the form of its quaternary ammonium derivative. Such quaternary ammonium compounds include those having the general formula:

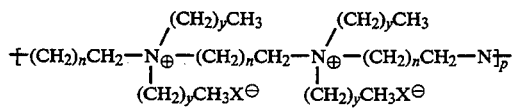

where
$0 \leq n \leq 20$;
$0 \leq y \leq 20$;
$p \geq 1$;
X is selected from the group consisting of functionalities having the formula Cl, Br, and I.

Suitable buffer compositions are liquid solutions of a multi-valent inorganic or organic buffering salt having a multi-varient charge which is opposite the charge on the organic coating. These multi-valent buffers include phosphate buffers, borate buffers, carbonate buffers, dicarboxylic acid buffers, and tricarboxylic acid buffers. Preferred buffer compositions include aqueous solutions of phosphate pH buffers such as combinations of monobasic phosphate and dibasic phosphate.

The methods of the present invention have particular utility in the electrophoretic separation of analytes having amino and amino derivative functionalities. Exemplary analyte compounds include amines, amino acids, peptides and their derivatives such amine hydrochlorides. By varying the electroosmotic flow in accordance with the teachings herein the electrophoretic separation and resolution of these analytes can be enhanced.

These and other advantages associated with the present invention will become apparent to those skilled in the art upon an understanding the invention as described in the detailed description of the invention taken in combination with the following drawings.

DETAILED DESCRIPTION OF THE INVENTION

Figure 1:
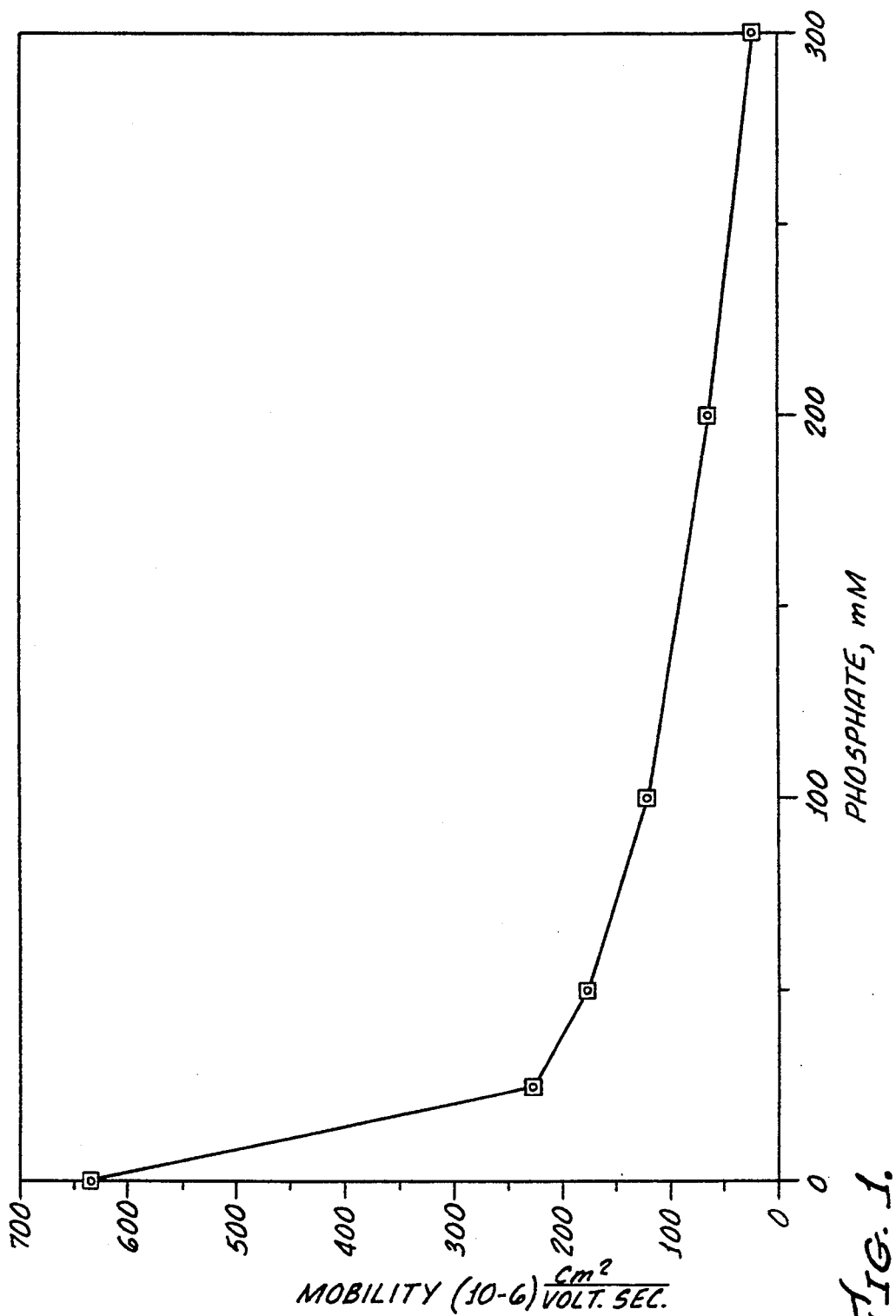
FIG. 1 is a plot of the mobility of a neutral marker compound, benzyl alcohol, versus buffer compound concentration. The mobility data was obtained utilizing a capillary column coated on its interior surface with a charged polyamine.

The present invention provides methods for varying the electroosmotic flow in capillary electrophoresis columns having ionically charged coatings on their interior surface. The practice of the present invention is particularly useful in electrophoretic separation systems such as the P/ACE series Capillary Electrophoresis Systems manufactured and sold by Beckman Instruments, Inc., Fullerton, Calif.

The methods for varying electroosmotic flow of the present invention are useful tools in the separation of a variety of molecular species on the basis of their electrophoretic mobility. These molecular species include macromolecules such as proteins and polynucleotides as well as smaller compounds such as basic drugs and nucleic acids.

The invention described herein provides user control of electroosmotic flow and is preferably practiced when the ability to manipulate or change electroosmotic flow for a particular electrophoresis column will enhance or improve analytical separations. Because coated capillary electrophoresis columns are utilized in combination with the ability to increase or decrease electroosmotic flow, the present invention quite unexpectedly and advantageously provides the benefits of coated columns and uncoated columns.

The methods described herein provide for controlling electroosmotic flow in a capillary electrophoresis column in order to enhance the electrophoretic resolution of components in a sample during electrophoresis. An exemplary method includes first providing a capillary column fabricated of a length of tubing having an interior surface coated with an organic ionic compound. The coated column also provides a characteristic electroosmotic flow during electrophoretic separation conditions using an electrophoretic buffer composition having a first multi-valent buffer concentration. The next step involves introducing a buffer composition which includes a multi-valent compound into the coated capillary column. The buffer composition has a second multi-valent buffer compound concentration such that to increase the electroosmotic flow the second multi-valent buffer compound concentration is smaller than the first multi-valent buffer concentration, and to decrease the electroosmotic flow the second multi-valent buffer compound concentration is greater than the first multi-valent valent buffer concentration. Then introducing the sample composition into an end of the length of tubing and applying an electric field across a cathode reservoir positioned at one end of the tubing and an anode reservoir positioned at the other end of the tubing causes the electroosmotic flow to vary from the electroosmotic flow characteristic of the coated column.

The capillary tubing can be fabricated of any material having physical and chemical properties suitable for capillary tubing and having charged chemical functionalities on its surface. In preferred embodiments of the present invention, the capillary tubing is fabricated of silica containing glass and the charged chemical moieties are silanol functionalities, $SiO^{-1}$, which are easily formed upon exposing the surface of fused silica to even slightly basic solutions. As known in the art of capillary separation systems, the capillary tubing can vary in length and in diameter, each of which depends upon the particular analytical application. Typically the column will be from between about 10 cm to 200 cm in length and from 25–200 μm in inner diameter.

In accordance with the present invention the capillary interior wall has a coating of an organic ionic compound which includes chemical entities which carry a charge opposite to the charge carried by the interior surface wall of the capillary column. Because preferred columns carry a negative charge, preferred organic ionic compounds are positively charged compounds such as amines or polyamines in the form of their quaternary ammonium derivative. Multi-valent ionic compounds are preferred, such as polyamines. These compounds are generally represented by the formula:

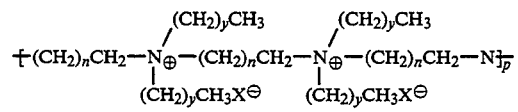

where
$0 \leq n \leq 20$;
$0 \leq y 20$
$p \geq 1$;
X is selected from the group consisting of functionalities having the formula Cl, Br, and I;

Especially preferred organic multi-valent ionic compounds are crosslinked with a crosslinking reagent having at least two functionalities reactive with functionalities present on the multi-valent ionic compound. Such compounds and their preparation as well as processes for preparing coated capillary columns are described in copending U.S. patent application Ser. No. 08/128,914 filed Sep. 29, 1993. An exemplary crosslinked multi-valent organic compound which provides enhanced physical integrity and interior column wall-coating interaction has the following general formula:

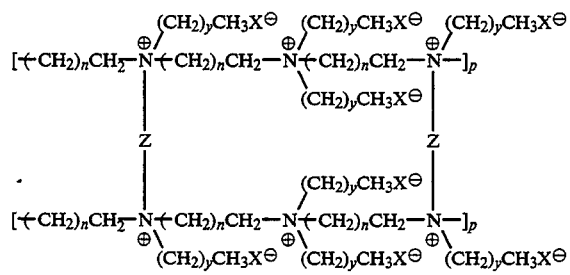

where
$0 \leq n \leq 20$;
$0 \leq y \leq 20$;
$p \geq 1$;
X is selected from the group consisting of functionalities having the formula Cl, Br, and I;
Z is an organic radical selected from the group consisting of functionalities having the formula:

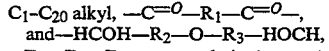

where $R_1$, $R_2$, $R_3$ are each independently $C_1$–$C_{20}$ alkyl.

Preferred crosslinked quaternary ammonium compounds are preferably prepared from polymeric amine compounds having molecular weights from about 1000 to about 100,000.

Those skilled in the art will appreciate that the positive charges on the quaternary ammonium compound interact with negative charges of the ionized silanol functionalities on the surface of the silica column and ionically bind to the interior surface of the capillary column. When the multi-valent charged compound is crosslinked, the increased molecular weight of the multi-valent ionic compound and the more tightly bond network of polymeric chains enhance the physical integrity of the coating and generally all for facile bonding to the surface of the capillary. The charge density of the organic ionic compound and the amount of coating should be sufficiently high to mask the charges on the interior surface of the capillary and interact with the charged chemical moieties on the surface of the capillary wall to form an ionically bound coating.

In accordance with the present invention suitable multi-valent buffer compositions include liquid solutions of multi-valent ionic compounds having pH buffering capabilities. Such compounds are known in the art, a restriction being that the pH buffer be multi-valent and that the multi-valent charge be opposite that of the charged coating on the interior surface of the capillary column. For capillary columns having charged amine coating on their interior surface, suitable multi-valent buffer compounds have multi-valent anionic characteristics. Those skilled in the art will appreciate that multi-valent pH buffers having these characteristics include phosphate buffers, borate buffers, carbonate buffers, dicarboxylic acid buffers such as maleates and succinates, and tricarboxylic acid buffers such as citrates. Preferred buffer compositions include aqueous solutions of phosphate pH buffers such as combinations of monobasic phosphate and dibasic phosphate.

Basically, the practice of the present invention involves improving electrophoretic analyses in the form of enhancing sample component resolution while keeping total sample analysis time at the minimum necessary to obtain the desired sample resolution. Moreover, the present invention requires no special equipment and common electrophoresis instrumentation and techniques are utilized. Thus, once a sample composition is subjected to electrophoretic separation conditions the electroosmotic flow characteristic of those condition can be varied. More particularly, by first obtaining an electropherogram using a capillary column with a charged coating and running buffers of any selected type and any concentration, the electroosmotic flow characteristic of those conditions can be varied in a subsequent electrophoresis analysis using the same column and a different type and/or concentration of a multi-valent running buffer. The multi-valent buffer concentration is selected to increase or decrease electroosmotic flow so that the resolution, migration time, and number of identified components in the analytical sample (proteins, basic drugs, peptides, oligonucleotides, nucleic acids, etc.) is optimized.

For example, if a mixture of proteins for analysis is first separated into its component proteins using a capillary column coated with a charged polyamine and a buffer composition of monovalent buffer compound such as Hepes running buffer, the electroosmotic flow is relatively high and the migration time of each of the components relatively fast. In many instances, the high electroosmotic flow precludes effective electrophoretic migration and resolution of the sample components. If the same sample is then subjected to electrophoretic conditions using a buffer composition prepared from a multi-valent buffer, unexpectedly, the electroosmotic flow decreases, and resolution increases. Increasing the concentration of the multi-valent buffer in the buffer composition further decreases electroosmotic flow and causes an increase in the resolution of the sample components.

Similarly, if a mixture of proteins for analysis is first separated into its component proteins using a capillary column coated with a charged polyamine and a buffer composition having a relatively low concentration of multi-valent buffer compound such as 5–10 mM phosphate buffer at a suitable pH, the electroosmotic flow is relatively high and the migration time of each of the components relatively fast. If the same sample is then subjected to electrophoretic conditions using a buffer composition having an increased concentration of the multi-valent buffer, unexpectedly, the electroosmotic flow decreases, and resolution increases.

It is believed that multi-valent compounds are capable of interacting or ionically complexing with the charged functionalities of organic coating on the interior wall of the column thereby masking the coating charge. Since the coating charge is primarily responsible for the relatively high electroosmotic flow associated with the charged cationic coatings, masking the coating in this way results in a reduced electroosmotic flow under electrophoretic conditions. Increasing the concentration of multi-valent buffer compound in the running buffer composition for a subsequent analysis produces a corresponding decrease in electroosmotic flow. This is probably due to an even higher degree of masking of the charge on the coating, a phenomenon which does not occur when mono-valent buffer compounds are the running buffer.

Thus, the present invention, provides processes for varying electroosmotic flow in a capillary columns having charged coatings. In order to increase electroosmotic flow obtained using a buffer composition having particular concentration of a multi-valent buffer compound in the coated capillary column, one need only to decrease the concentration of the multi-valent buffer compound in the buffer composition. Similarly, in order to decrease the electroosmotic flow, one need only to increase the concentration of the multi-valent buffer compound. Finally, when the use of a buffer composition of mono-valent buffer compound results in electrophoretic conditions having an electroosmotic flow which is too high, use of a running buffer of multi-valent buffer compound decreases the electroosmotic flow.

As already mentioned, the electrophoresis methods described herein take advantage of known electrophoresis methods and instrumentation. Thus, the steps of introducing buffer compositions in electrophoresis capillaries, introducing a sample composition into the interior of the coated column at one end and applying an electric field across anodic reservoirs and cathodic reservoirs are well within the ability of those skilled in the art. When a suitable detector, for example a uv-visible detector or fluorescence detector, is appropriately positioned at least one end of the coated column, the separated sample constituents are detected and an electropherogram is generated.

The following examples are offered as being illustrative of exemplary embodiments of the present invention. These examples are non-limiting and are offered as exemplary only.

EXAMPLE 1

The following example illustrates the preparation of a crosslinked polymeric alkyl amine or polyamine (PEI) suitable for use in processes of the present invention and having.

A variety of different molecular weights of PEI is available from about 160 to about 1,000,000 and having the general formula:

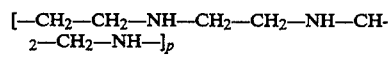

The procedure described below is applicable to the preparation of crosslinked PEI1800, PEI 1200, and PEI 600 as well as a variety of multi-valent amines having similar molecular weight properties.

A 10 g portion of PEI 1800 was add to a solution of 20 mL of methanol and 300 mL of tetrahydrofuran. After the PEI was completely dissolved, a 1.0 g portion of butadiene diepoxide was added to the PEI solution. The resulting solution of PEI and butadiene diepoxide was refluxed for 16 hours then allowed to cool to room temperature. Then 100 mL of water was added to the cooled solution and the methanol and tetrahydrofuran solvents were evaporated from the solution in a rotary evaporator under reduced pressure. The remaining aqueous solution of crosslinked PEI is suitable for use in a subsequent alkylating procedure.

EXAMPLE 2

The following example is illustrative of a procedure for crosslinking low molecular weight multi-valent amines. The described procedure was used interchangeably to crosslink pentaethylenehexamine and triethylenetetramine, having 6 and 4 amine functionalities, respectively.

A 10 gram portion of either pentaethylenehexamine or triethylenetetramine was added to 200 mL of tetrahydrofuran. After the amine was completely dissolved a 1 g portion of butadiene diepoxide was added to the tetrahydrofuran solution and the resulting diepoxide and amine solution was refluxed for 16 hours. The refluxed solution was allowed to cool to room temperature and then 100 mL of water was added to the cooled solution. The tetrahydrofuran portion of the solvent was evaporated on a rotary evaporator under reduced pressure and the resulting aqueous solution of crosslinked amine was suitable for use in an alkylating reaction.

EXAMPLE 3

The following example illustrates a typical method suitable for alkylating crosslinked polymeric amines and smaller crosslinked amine compounds, including the crosslinked PEI's and crosslinked pentaethylenehexamine and triethylenetetramine described above. Although iodomethane is the alkylating reagent utilized in this example, a large number of alkylating agents, including chloro and bromo alkyl compounds are interchangeable with the iodomethane.

A 200 mL volume of methanol, 30 g of sodium carbonate, 100 mL of water, and 50 mL of iodomethane were added to an aqueous solution containing 10 grams multi-valent amine compound crosslinked as described in EXAMPLE 1 or EXAMPLE 2. The reaction mixture was allowed to reflux for 16 hours and the methanol was removed using a rotary evaporator under reduced pressure. The resulting quaternary ammonium compound aqueous solution was diluted to 1000 mL total volume and then filtered through of 0.45 μm pore size filter. This filtered solution is suitable for applying to the interior surface of capillary tubing in order to form an ionically interacting coating.

EXAMPLE 4

The following example is exemplary of methods suitable for preparing capillary tubing and methods for forming the coating on the interior surface of the tubing in order to provide the final coated capillary column.

The interior surfaces of a length of 50 μm diameter capillary tubing purchased from Polymicro of Phoenix, Arizona was rinsed with a solution of 1N HCl for 15 minutes. The HCl solution was removed and the interior of the tubing was rinsed with a 1N solution of NaOH for 15 minutes which was followed by a clear water rinse for 15 minutes. Then the prepared length of capillary column was rinsed for 15 minutes with an aqueous solution containing about 1% by weight of crosslinked quaternary ammonium compound. Following this rinsing step the coated capillary column was suitable for use in standard capillary electrophoresis procedures.

EXAMPLE 5

The following experiment illustrates the dramatic and unexpected variation in electroosmotic flow obtained by varying the concentration of a running buffer prepared of multi-valent buffer compound.

In order to demonstrate the effect of varying the concentration of multi-valent buffer compounds utilizing a polyamine coated capillary electrophoresis column, the migration of a neutral marker compound, was determined. Because neutral marker compound do not carry a charge, they do not electrophoretically migrate. Thus, under electrophoresis conditions, the movement of these neutral marker compounds through columns is due only to electroosmotic flow within the coated capillary electrophoresis column.

The experiments were carried out by preparing a 10 μl/mL aqueous solution of benzyl alcohol, a neutral marker, and subjecting the aqueous solution to several electrophoresis runs using a capillary coated with a polyamine in the form of a quaternary ammonium compound. The experiments were carried out on a P/ACE Electrophoresis Instrument (Beckman Instruments, Fullerton, Calif.) using a 254 nm detection. The column had an overall length of 27 cm and an effective length of 20 cm. The electric field applied was 8.10 kV. The benzyl alcohol solution sample was introduced in to the column using a 2 second pressure injection. The first electrophoresis run utilized a HEPES, monovalent buffer, to establish a first characteristic migration time. Subsequent electrophoresis runs utilized equal molar concentrations of multi-valent monobasic phosphate buffer and dibasic phosphate at varying total phosphate concentrations (pH 7.0). The migration time for the benzyl alcohol was measured for each analysis and the mobility vs multi-valent buffer concentration was determined for each electrophoresis run.

The running buffers and their concentrations for each run were as follows:

| RUN | Buffer | Concentration |
| --- | --- | --- |
| 1 | HEPES | 50 mM, pH 7.0 |
| 2 | Phosphate | 25 mM, pH 7.0 |
| 3 | Phosphate | 50 mM, pH 7.0 |
| 4 | Phosphate | 100 mM, pH 7.0 |
| 5 | Phosphate | 200 mM, pH 7.0 |
| 6 | Phosphate | 300 mM, pH 7.0 |

FIG. 1 illustrates the results of this experiment. Clearly, by increasing the concentration of a multi-valent buffer compound (phosphate buffer) having a multi-valent charge opposite that of the cationically charged polyamine coating, the mobility of the neutral marker decreases. When a monovalent buffer is utilized, at a relatively high concentration, the electroosmotic flow and neutral marker mobility is not effected.

EXAMPLE 6

Figure 2:
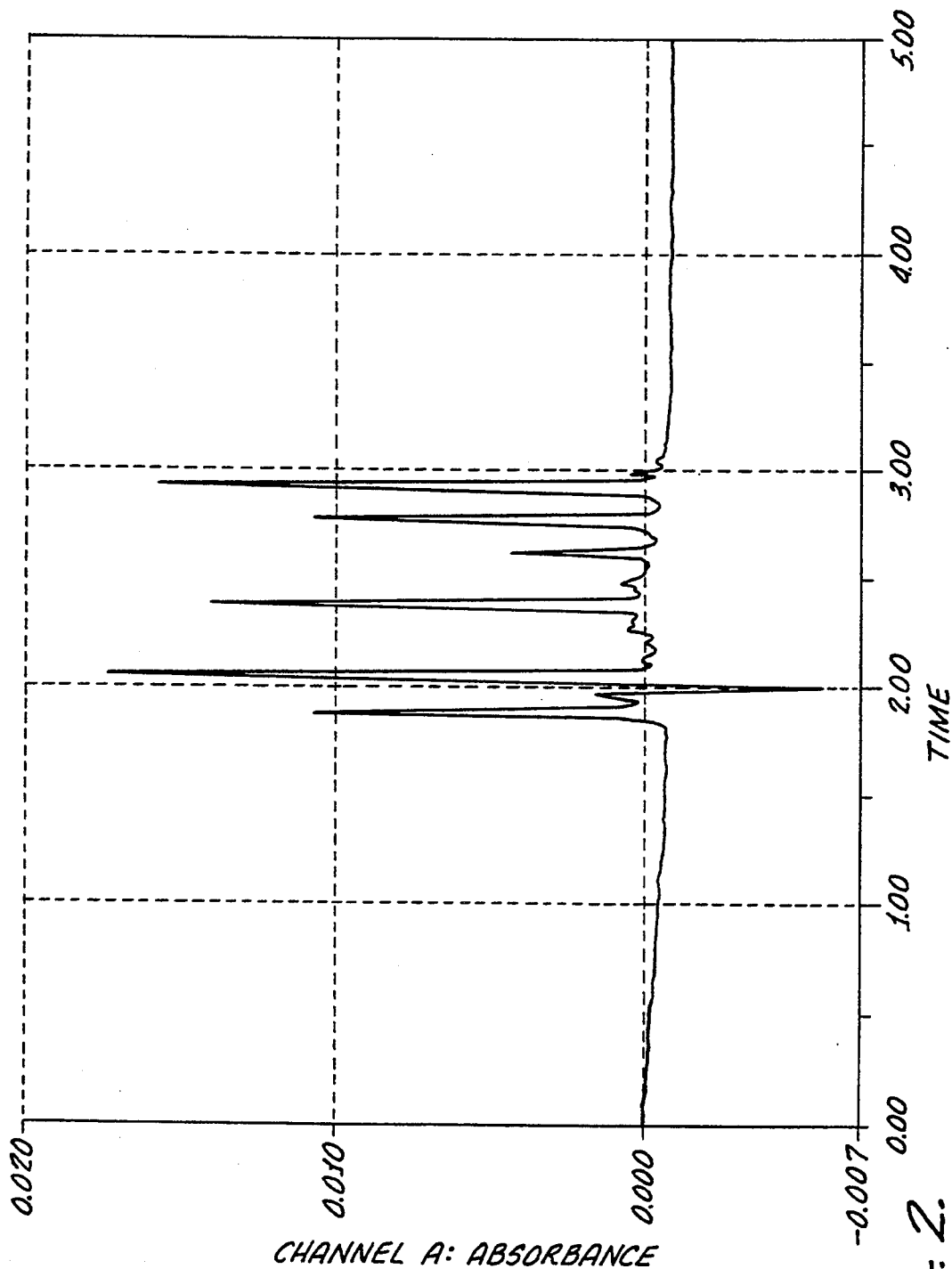
FIG. 2 is an electropherogram of a mixture of proteins separated utilizing a 50 mM Hepes buffer at pH 7.0 in a charged polyamine coated capillary column.
Figure 3:
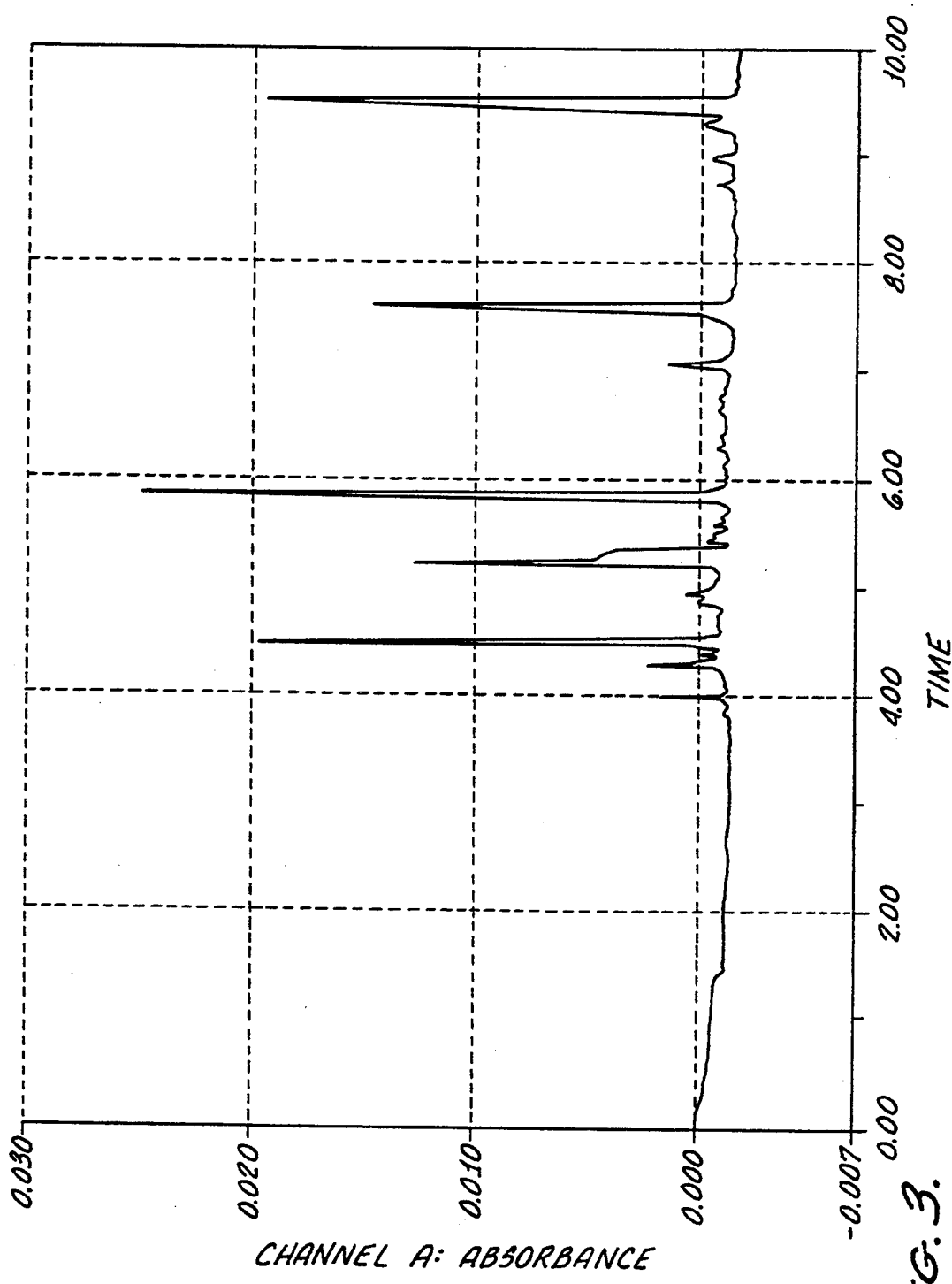
FIG. 3 is an electropherogram of the same mixture of proteins as that separated as shown in FIG. 2 utilizing a 25 mM phosphate buffer (equal molar dibasic phosphate and monobasic phosphate) in a capillary column coated on its interior surface with a charged polyamine.
Figure 4:
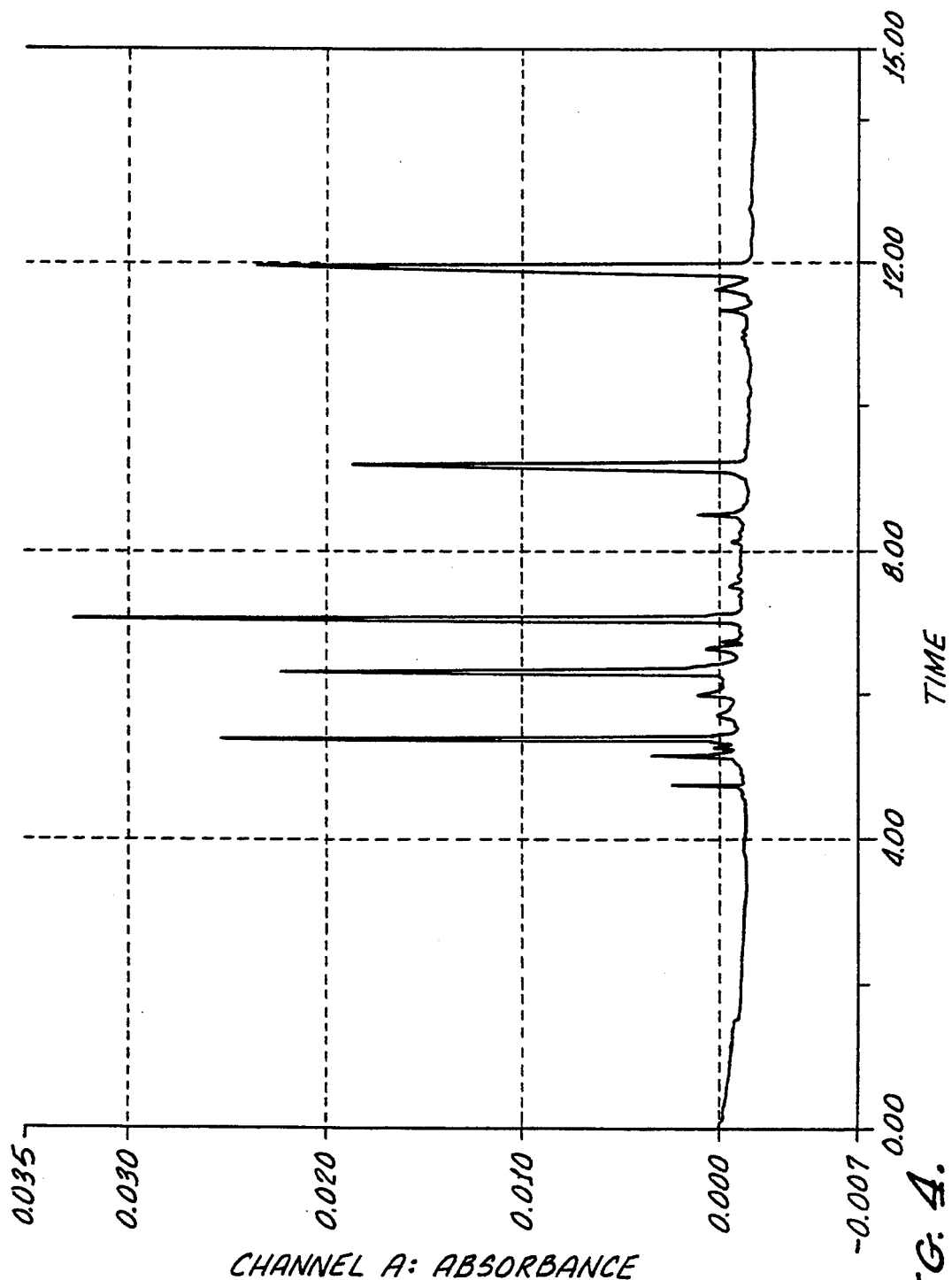
FIG. 4 is an electropherogram of the same mixture of proteins as that separated as shown in FIG. 2 and 3, utilizing a 50 mM phosphate buffer (equal molar dibasic phosphate and monobasic phosphate) in a capillary column coated on its interior surface with a charged polyamine.

The following illustrates exemplary procedures for increasing or decreasing electroosmotic flow utilizing capillary columns having interior walls coated with charged polyamines. A 30 cm overall capillary column having a crosslinked polyamine in the form of a quaternary ammonium compound was positioned in a P/ACE capillary electrophoresis instrument (manufactured by Beckman Instruments, Inc., Fullerton, Calif.). A sample containing 1 mg/mL of carbonic anhydrase, myoglobin, ribonuclease A, cytochrome C and lysozyme was prepared. An aliquot of the sample was subjected to capillary electrophoresis four times using a different concentration of running buffer. For each electrophoresis run, the sample was injected using a 3 second pressure injection, a voltage of 14.8 kV applied across the reservoirs and a 214 nm ultra-violet detection. FIG. 2-5 show the electropherograms which were obtained for each run. FIG. 2 is that of a separation using 50 mM HEPES buffer at pH 7.0. FIG. 3 was obtained using 25 mM phosphate buffer at pH 7.0. FIG. 4 was obtained using 50 mM phosphate buffer, and FIG. 5 was obtained using 100 mM phosphate buffer. In all of the electropherograms the order of protein migration from left to right is carbonic anhydrase, myoglobin, ribonuclease A, cytochrome C, and lysozyme.

Figure 5:
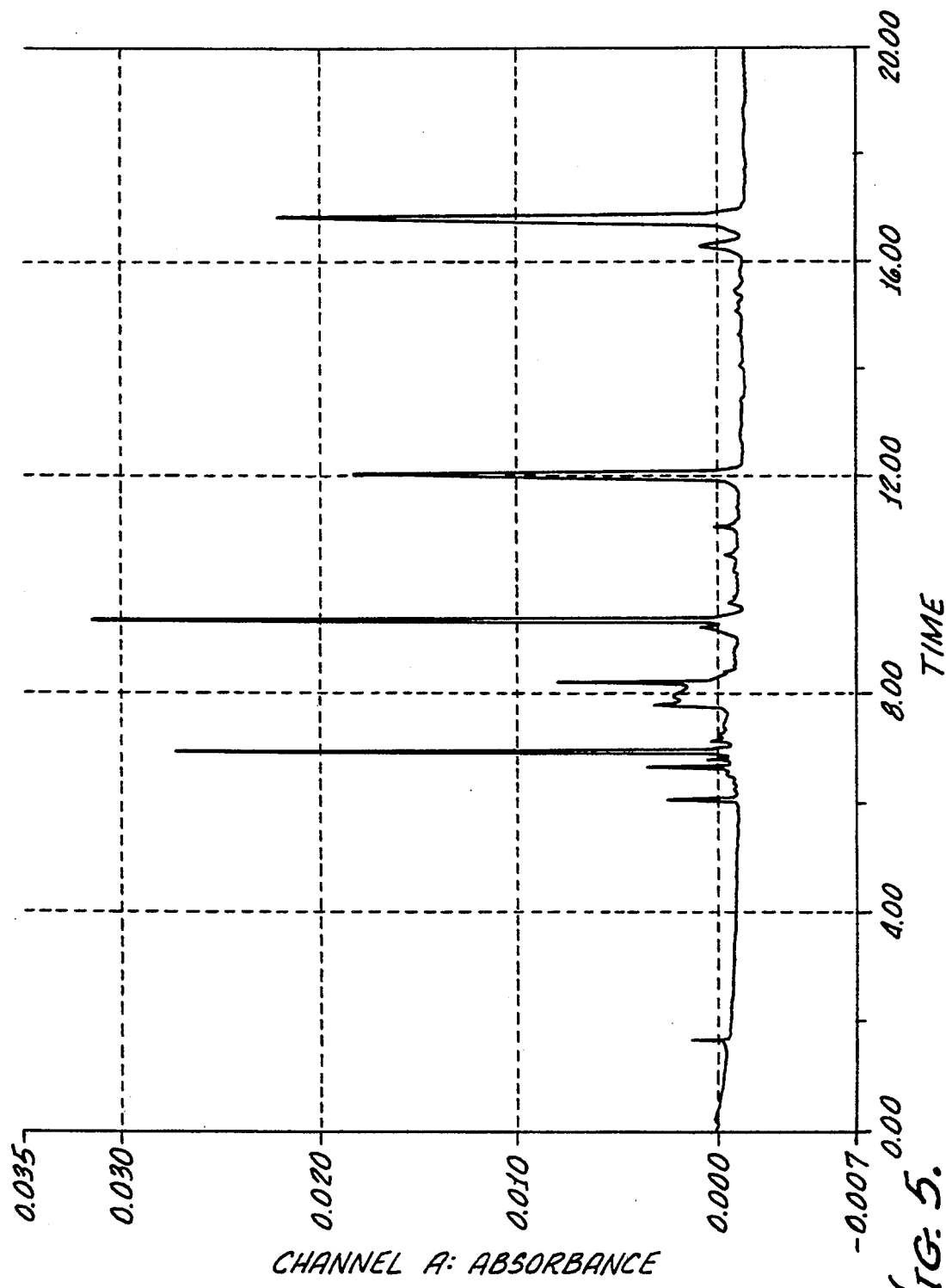
FIG. 5 is an electropherogram of the same mixture of proteins as that separated as shown in FIG. 2, 3 and 4, utilizing a 100 mM phosphate buffer (equal molar dibasic phosphate and monobasic phosphate) in a capillary column coated on its interior surface with a charged polyamine.

The electropherograms illustrate the dramatic and unexpected effect of changing the concentration of a multi-valent buffer. In FIG. 2 the total a migration time is 3 minutes using a mono-valent buffer HEPES which maintains a relatively high electroosmotic flow. When a multi-valent phosphate buffer is utilized (FIG. 3), even at a lower concentration, the electroosmotic flow decreases and the migration time increases to 10 minutes. FIG. 4 and FIG. 5 similarly show a dramatic decrease in electroosmotic flow and increase in migration time with an increase in phosphate buffer concentration.

What is claimed is:

1. A method for controlling electroosmotic flow in a capillary electrophoresis column, said method comprising the steps:

providing a capillary column comprising a length of tubing having an interior surface coated with an organic multi-valent ionic compound, said coated capillary column having a characteristic electroosmotic flow during electrophoretic separation conditions using an electrophoretic buffer composition having a first multi-valent buffer concentration;

immersing one end of said capillary column in an anodic reservoir and immersing a second end of said capillary column in a cathodic reservoir;

introducing a composition comprising a multi-valent buffer compound into said capillary, said composition having a second multi-valent buffer compound concentration such that to increase said electroosmotic flow said second multi-valent buffer compound concentration is smaller than said first multi-valent buffer concentration, and to decrease said electroosmotic flow said second multi-valent buffer compound concentration is greater than said first multi-valent buffer concentration;

introducing a sample composition having at least one sample constituent into said length of capillary tubing at said first end or said second end; and applying an electric field across said reservoirs, said electric field capable of causing said at least one sample constituents to migrate within said capillary, wherein said electroosmotic flow varies with said second multi-valent buffer concentration.

2. The method of claim 1 wherein said at least one sample constituents are selected from the group consisting of peptides, proteins, and amines.

3. The method of claim 1 wherein said multi-valent buffer compound has a multi-valent charge opposite to said charged organic coating.

4. The method of claim 1 wherein said multi-valent buffer compound is selected from the group consisting of phosphate buffers, borate buffers, dicarboxylic acid buffers, tri-carboxylic acid buffers.

5. The method of claim 1 wherein said first and second multi-valent buffer concentration is from 0 to about 500 mM.

6. The method of claim 1 wherein said organic multi-valent ionic compound comprises polymeric quaternary ammonium compound derivative of polyamine.

7. The method of claim 6 wherein said quaternary ammonium compounds includes compounds having at least three quaternary ammonium functionalities.

8. The method of claim 3 wherein said quaternary ammonium compound is selected from the group consisting of compounds having the formula:

$$\dagger(CH_2)_nCH_2-\overset{(CH_2)_yCH_3}{\underset{(CH_2)_yCH_3X^\ominus}{N_\oplus}}-(CH_2)_nCH_2-\overset{(CH_2)_yCH_3}{\underset{(CH_2)_yCH_3X^\ominus}{N_\oplus}}-(CH_2)_nCH_2-N\dagger_p$$

where
  $0 \leq n \leq 20$;
  $0 \leq y \leq 20$;
  $p \geq 1$;
  X is selected from the group consisting of functionalities having the formula Cl, Br, and I.

9. A method for decreasing electroosmotic flow in a capillary electrophoresis column, said process comprising the steps:

providing a capillary column comprising a length of tubing having an interior surface coated with an organic multi-valent ionic compound, said coated capillary column having a characteristic electroosmotic flow during electrophoresis conditions using an electrophoretic buffer composition comprising a mono-valent buffer compound;

immersing a first end of said capillary column in an anodic reservoir and immersing a second end of said capillary column in a cathodic reservoir;

introducing a composition comprising a multi-valent buffer compound into said capillary, introducing a sample composition into said length of capillary tubing at said first end or said second end; and applying an electric field across said reservoirs, whereby said composition of multi-valent buffer compound causes said coated capillary column to have a multi-valent buffer electroosmotic flow less than said characteristic electroosmotic flow.

10. The method of claim 9 wherein said multi-valent buffer compound has a multi-valent charge opposite to said charged organic coating.

11. The method of claim 9 wherein said multi-valent buffer compound is selected from the group consisting of phosphate buffers, borate buffers, dicarboxylic acid buffers, tri-carboxylic acid buffers.

12. The method of claim 9 wherein said first and second multi-valent buffer concentration is from 0 to about 500 mM.

13. The method of claim 9 wherein said organic multi-valent ionic compound comprises polymeric quaternary ammonium compound derivative of polyamine.

14. A method for enhancing the analysis of a sample composition for sample constituents by capillary electrophoresis, said process comprising the steps:

providing a capillary electrophoresis column comprising:
a length of capillary tubing having an interior surface, having charged chemical functionalities a first end, and a second end, said interior surface having a coating on said interior surface, said coating comprising crosslinked organic multi-valent ionic compounds capable of ionic interaction with said charged chemical functionalities of said interior surface;

introducing a running buffer composition into said capillary tubing said running buffer composition comprising a multi-valent buffer compound having a first buffer concentration, said running buffer composition providing said column with a first electroosmotic flow;

introducing said sample composition having at least one charged sample constituent into said length of capillary tubing at said first end or said second end;

applying an electric field across said reservoirs;

determining if sample constituents of said sample composition are sufficiently resolved;

introducing a second buffer composition having a multi-valent buffer compound and a second multi-valent buffer compound concentration selected so that to increase electroosmotic flow and decrease sample constituent migration time said second multi-valent buffer concentration is less than said first buffer concentration, and to decrease electroosmotic flow and increase sample constituent migration time said second multi-valent buffer concentration is greater than said first buffer concentration; and applying an electric field across said reservoirs to obtain an enhanced sample constituent analysis.

15. The method of claim 14 wherein said multi-valent buffer compound has a multi-valent charge opposite to said charged organic coating.

16. The method of claim 14 wherein said multi-valent buffer compound is selected from the group consisting of phosphate buffers, borate buffers, dicarboxylic acid buffers, tri-carboxylic acid buffers.

17. The method of claim 14 wherein said first and second multi-valent buffer concentration is from 0 to about 500 mM.

18. The method of claim 14 wherein said organic multi-valent ionic compound comprises polymeric quaternary ammonium compound derivative of polyamine.

* * * * *